United States Patent [19]

Knowlton

[11] 4,385,121

[45] May 24, 1983

[54] MEDIUM AND PROCESS FOR DISPOSING OF HYDROCARBON WASTES

[75] Inventor: Harold E. Knowlton, Moraga, Calif.

[73] Assignee: Chevron Research Company, San Francisco, Calif.

[21] Appl. No.: 309,483

[22] Filed: Oct. 7, 1981

[51] Int. Cl.³ .......................... C12N 1/00; C12N 1/26; C12N 1/28; C12N 1/38

[52] U.S. Cl. .................... 435/244; 435/248; 435/249; 435/253; 435/262; 210/610; 210/611

[58] Field of Search ............... 435/244, 248, 249, 250, 435/253, 262, 281, 264; 210/610, 611

[56] References Cited

U.S. PATENT DOCUMENTS

| | | | |
|---|---|---|---|
| 2,769,750 | 11/1956 | Harris | 435/248 |
| 2,813,821 | 11/1957 | Updegraff | 435/254 |
| 3,152,983 | 10/1964 | Davis et al. | 210/611 |
| 3,224,946 | 12/1965 | Raymond | 435/244 |
| 3,616,204 | 10/1971 | Linn | 435/244 |
| 3,843,517 | 10/1974 | McKinney et al. | 435/281 |

FOREIGN PATENT DOCUMENTS 55-137186  10/1980  Japan .................................. 435/253

*Primary Examiner*—Esther M. Kepplinger
*Attorney, Agent, or Firm*—Burns, Doane, Swecker & Mathis

[57] ABSTRACT

An improved landfarming medium and process is disclosed in which hydrocarbon wastes are disposed of by dispersing them in a medium composed of a mixture of soil containing hydrocarbon-oxidizing microorganisms and a spent, solid, particulate, porous hydrocarbon cracking catalyst and/or a spent, solid, particulate, porous filtration medium.

8 Claims, No Drawings

MEDIUM AND PROCESS FOR DISPOSING OF HYDROCARBON WASTES

BACKGROUND OF THE INVENTION

1. Field of the Invention

The invention is in the field of hydrocarbon waste disposal. More particularly, the invention relates to a landfarming medium and process in which waste hydrocarbons are oxidized by microorganisms.

2. Description of the Prior Art

It is well-known that hydrocarbon-utilizing microorganisms are ubiquitous in soil. These microorganisms use hydrocarbons as an energy source for their life processes and frequently as a source of cell structural materials. The reactions by which the organisms metabolize hydrocarbons are enzyme-catalyzed oxidations involving dehydrogenation of the hydrocarbon substrate. The process is called aerobic metabolism when the hydrogen atoms generated in the reaction are combined with oxygen to form water and anaerobic metabolism when the hydrogen atoms are combined with hydrogen-accepting moieties other than oxygen, such as nitrate or sulfate. The ability of microorganisms to oxidize hydrocarbons has been used widely to treat hydrocarbon-containing wastes.

The patent literature describes various microbial processes for disposing of hydrocabon wastes. U.S. Pat. No. 3,152,983 describes a process for treating aqueous hydrocarbon-containing wastes by adding a microbial sludge to the waste and aerating the waste. The microbes oxidize the hydrocarbons in the waste. U.S. Pat. No. 3,224,946 teaches a process for enhancing microbial attack of hydrocarbons in an aqueous medium. The enhancement involves adding finely divided zeolitic molecular sieves to the medium. The hydrocarbon substrate is absorbed by the sieves, thus dividing it into small occluded particles and facilitating its oxidation by the microbes in the medium.

U.S. Pat. No. 3,616,204 concerns a technique for treating accidental oil spills on soil by tilling the oil into the soil, inoculating the soil with a hydrocarbon oxidizing microorganism, and adding nutrients to the soil and maintaining its oxygen content to stimulate microbial oxidation of the oil. U.S. Pat. No. 3,843,517 relates to a similar technique for eliminating oil slicks on bodies of water. The technique involves dispersing lyophilized cultures of oil-consuming microorganisms adsorbed on porous carriers in the oil slick.

The ability of soil microorganisms to consume or ferment hydrocarbons is also used to dispose of hydrocarbon wastes in a process called "landfarming" or "land spreading". In landfarming the hydrocarbon waste is tilled, injected or otherwise incorporated into the soil. Once in the soil, the hydrocarbon is oxidized by soil microorganisms into innocuous products such as carbon dioxide, water, and humus. It is often necessary to till the soil frequently to aerate it to provide the oxygen necessary for the fermentation. The main problem with current landfarming is that it requires a substantial land area for a substantial time period to dispose of a large volume of hydrocarbon. There is, therefore, a great need for increased biodegradation rate in landfarming so that less land area is required per unit amount of disposed hydrocabon. The present invention is directed to filling that need.

SUMMARY OF THE INVENTION

One aspect of the invention is a medium for disposing of hydrocarbon wastes comprising a mixture of soil containing hydrocarbon oxidizing microorganisms and at least one of either a spent, solid, particulate porous, hydrocarbon cracking catalyst or a spent, solid, porous, particulate filtration medium.

Another aspect of the invention is a process for disposing of hydrocarbon wastes comprising dispersing the waste in said medium under conditions that stimulate the oxidation of the waste by said microorganisms.

DETAILED DESCRIPTION OF THE INVENTION

As used herein the term "hydrocarbon" as used to describe the waste is intended to include not only substrates that are composed of only carbon and hydrogen but also any organic substrate that is oxidized by soil microorganisms. This term includes, therefore, without limitation, saturated and unsaturated aliphatic hydrocarbons, saturated and unsaturated cycloaliphatic hydrocarbons, aromatic hydrocarbons, heterocyclic compounds, carboxylic acids, aldehydes, hydroxylated hydrocarbons, chlorinated hydrocarbons, carbohydrates, carboxylic esters, and proteins. The process is particularly useful for disposing of waste oils of mineral or vegetable origin such as those produced in the refining or use of petroleum, shale, tar sand, coal, or vegetable oils.

The medium into which the hydrocarbon wastes are incorporated comprises soil containing the microorganisms and a spent hydrocarbon refining catalyst and/or filtration media. The proportions of these two components in the mixture may vary widely. Typically the volume ratio of soil to spent catalyst and/or filtration media will be in the range of about 9:1 to 1:9. Minor amounts of nitrogen sources, such as ammonium nitrate and sodium nitrate, phosphate sources such as sodium or potassium hypophosphate, and trace minerals may be added to the mixture if the indigenous quantities of same in the soil are not sufficient to sustain the microorganisms and stimulate the desired degree of microbial growth. Buffering agents may also be added, if necessary, to adjust the pH of the medium to that which is optimal for microorganism activity.

Although the particular nature of the soil used in the medium is not critical, loam, sandy loam or sandy soils are preferred. Most natural soils contain sufficient quantities of hydrocarbon-oxidizing microorganisms to provide an adequate initial microbe population in the medium. If, however, a sterilized soil or soil having a low microbe count is used, it may be necessary to inoculate the soil with hydrocarbon-oxidizing microorganisms. Such soil microorganisms include protozoa, bacteria, yeasts, and molds. In this regard bacteria from the genera Clostridia Candida, Thiobacillus, Pseudomonas, Desulfovibrio, Micrococcus, Aerobacter, Sarcina, Saratia, Bacterium, Bacillus, Mycobacterium Nocardia, and Actinomyces are known to be particularly effective in oxidizing hydrocarbons. Some bacteria oxidize hydrocarbons selectively and, depending upon the particular hydrocarbons being disposed of, it may be desirable to employ a medium having a high count of bacteria of a genus or of genera that are particularly effective in oxidizing such hydrocarbons. For instance, many bacteria of the genus Nocardia selectively oxidize paraffins.

The spent catalysts that are mixed with the soil are obtained from catalytic hydrocarbon cracking processes. Such catalysts are well-known and widely used. They are composed of natural or synthetic clays. The filter media that are alternatively used are of similar composition and will usually be composed of clays or earthen materials such as diatomaceous silica, expanded perlite, carbon, gypsum, magnesia, and fuller's earth. These catalysts and filter media are in a particulate form, usually cylindrical pellets or spheres or powders (e.g. cracking fines) whose largest dimension is less than about one cm, usually less than one-half cm. They are highly porous and normally have high surface areas (measured by the BET technique) in the range of 100 to 500 $m^2/g$. In their spent or used condition the catalyst will typically contain residual carbonaceous material, sulfur, and metal contaminants. In normal refining or filtering operations, these spent catalysts and filter media are usually disposed of after they become nonregenerable and have little or no value. Accordingly, the present invention provides a practical and worthwhile utility for such used hydrocarbon processing catalysts and filter media.

The catalyst or filter medium may be mixed with the soil before or after the hydrocarbon waste is added. In the field the hydrocarbon waste is at least partly adsorbed on the catalyst or filter media particles and is thus more completely dispersed in the medium in a manner in which it has a greater surface area for contact with the microbes and the oxygen needed for the effective oxidation. It is believed that biodegradation occurs at an interface containing moisture, water, air and microbes and the porous catalyst/filter medium increases the available interfacial area. The amount of liquid hydrocarbon waste incorporated into the medium will usually be in the range of one to 500 ml/kg. In landfarming it will be most convenient to till or inject the spent catalyst and waste, either separately or as a combined slurry, into the field soil using available tilling or injecting machinery. Preferably the application is made to a soil depth of less than about 30 cm since the microorganism population and oxygen content usually decreases with soil depth.

The most important conditions involved in microbial fermentation of hydrocarbon wastes are pH, temperature, and the availability of oxygen (except for anaerobes). In general, microorgansim oxidation occurs at pHs in the range of 5 to 9. Maximum activity typically occurs at approximately neutral pH (ca 7). As indicated previously buffer salts may be added to the medium to achieve optimum pH. Temperature influences not only the rate of microorganism activity but also affects the nature of the oxidation products since alternative metabolic reactions may be controlled by enzymes having different temperature optima. Optimal temperatures will vary with the nature of the microorganism population in the media and will normally be in the range of about 20° C. to 60° C. Optimal reaction rates for some hydrocarbon-oxidizing bacteria occur around 30° C. As a general rule, the amount of hydrocarbon oxidized by aerobes per unit time is increased by improving the oxygen supply to the medium. It is also important that sufficient oxygen be available to permit complete oxidation of the hydrocarbons. In this regard the invention provides a distinct advantage over prior landfarming techniques. The spent catalyst/filter medium, being highly porous, contains substantial amounts of water and oxygen that is available for use in the oxidation at the catalyst/filter medium surface. Also, because the catalyst is in the form of solid particles it facilitates natural aeration of the soil and inhibits soil compaction.

For the reasons stated above the oxidation of hydrocarbon wastes occurs more rapidly in the invention medium than in plain soil under comparable conditions. Under optimal fermentation conditions the majority of the oxidation reactions in the invention medium will usually be complete within less than a week. At that time additional waste may be added to the medium, if desired, without the need of adding more catalyst. It may, of course, be necessary to aerate or add more catalyst/filter medium after several waste application cycles.

The following hypothetical example further illustrates the invention. This example is not intended to limit the invention in any manner.

A sample of oil-exposed soil from a petroleum refinery is obtained. Microorganisms are cultured from the soil and identified by conventional procedures as including Bacterium aliphaticum and Nocardia paraffinae, species known to oxidize alkanes. The pH of the soil is 7.2. Five kg of this soil are mixed with one kg of a spent commerical petroleum silica cracking catalyst. One hundred ml of n-hexane are soaked into the soil-catalyst blend and the resulting mixture is placed in a closed fermentation chamber equipped with a $CO_2$ monitor. For comparison purposes an identical amount of n-hexane is incorporated into six kg of the soil and the hexane-laden soil is placed in another fermentation chamber. The chambers are maintained at 30° C. and the oxidations occuring therein are monitored by periodic measurement of the $CO_2$ content of the gas over the soil or soil-catalyst blend, as the case may be. After two weeks the oxidation of the hexane in the soil-catalyst blend is complete as evidenced by a leveling off of the $CO_2$ content in the gas above the blend. In comparison, after two weeks the $CO_2$ content of the gas above the plain soil is substantially less than that above the blend and is still increasing.

Modification of the above-described embodiments of the invention that are obvious to those of ordinary skill in the landfarming, hydrocarbon refining, microbiology, and related arts are intended to be within the scope of the following claims.

I claim:

1. A medium for disposing of hydrocarbon wastes comprising a mixture of soil containing hydrocarbon oxidizing microorganisms and at least one of a spent, solid, particulate, porous hydrocarbon cracking catalyst or a spent, solid, particulate, porous filtration medium, said spent catalyst or spent filtration medium containing at least one of carbonaceous, sulfur and metal residual material wherein the volume ratio of soil to catalyst or filtration medium is in the range of about 1:9 to 9:1.

2. The medium for disposing of hydrocarbon wastes of claim 1 wherein the microorganisms are predominantly bacteria.

3. The medium for disposing of hydrocarbon wastes of claim 1 wherein the surface area of the catalyst or filtration medium is in the range of 100 to 500 $m^2/g$.

4. The medium for disposing of hydrocarbon wastes of claim 1 wherein the pH of the mixture is in the range of 5 and 9.

5. The medium for disposing of hydrocarbon wastes of claim 1 wherein the pH of the mixture is approximately neutral.

6. The medium for disposing of hydrocarbon wastes of claim 1 wherein the mixture contains sufficient amounts of nitrogen and phosphate sources and trace minerals to support the microbes in the mixture.

7. A process for disposing of a hydrocarbon waste comprising dispersing the waste in the mixture of claim 1, 2, 3, 4, 5, or 6.

8. The process of claim 7 wherein the amount of waste is in the range of one to 500 ml per kg of said mixture.

* * * * *